United States Patent [19]
Saltarelli

[11] 3,936,272
[45] Feb. 3, 1976

[54] METHOD OF SEPARATING AND SCANNING ORGANIC CELLS AND MOLECULES

[76] Inventor: Cora G. Saltarelli, 316 Brentwood Road, Buffalo, N.Y. 14226

[22] Filed: Feb. 7, 1975

[21] Appl. No.: 547,946

[52] U.S. Cl. .............................. 23/230 B; 356/195
[51] Int. Cl.² .................. G01N 21/00; G01N 33/16
[58] Field of Search ................................. 23/230 B

[56] References Cited
OTHER PUBLICATIONS
Chemical Abstracts, 75: 6711c (1971).

Primary Examiner—Joseph Scovronek
Assistant Examiner—Sidney Marantz
Attorney, Agent, or Firm—Hill, Gross, Simpson, Van Santen, Steadman, Chiara & Simpson

[57] ABSTRACT

A method of separating and immobilizing constituent cells of heterogenuous intact organic cells and the molecular components of organic cells into bands in quartz tubes and scanning the bands with ultraviolet light to identify the cells by the degree in which they decrease the amount of transmitted light and the molecules by the wavelengths of light which they absorb. The method is useful in analyzing the cells of patients to determine a pathological condition, to predict a crisis in a patient undergoing therapy and to scan body fluids of normal individuals over a period of time to detect a pathological condition at a very early stage without the services of highly skilled technicians.

14 Claims, No Drawings

METHOD OF SEPARATING AND SCANNING ORGANIC CELLS AND MOLECULES

FIELD OF THE INVENTION

This invention relates to the art of organic cell analysis useful in diagnosing existing or developing pathological conditions in patients and specifically deals with a gradient system to develop patterns from biological materials that can be scanned for diagnosis of a pathological condition.

PRIOR ART

In an article entitled "Ultracentrifugation of Yeast Cells in a Gradient of Acrylamide Gel and Sucrose" by myself and others published in "Experientia" volume 25—1969 (Birkhauser Verlag Basel Switzerland), there is disclosed a technique for separating "starved" and "non-starved" yeast cells to provide a diagnostic or investigative tool indicating variation in cell parameters. This technique involves centrifuging in cellulose nitrate tubes to form a four layer gradient in a mixture of sucrose and acrylamide followed by photopolymerization with fluorescent light to immobilize the bands of cells in a gel. Such technique is limited to the scanning of cells or heavy precipitates due to the decrease in transmission of light and is ineffective to identify molecules in the cells or heavy precipitates.

SUMMARY OF THE INVENTION

According to this invention a sucrose-acrylamide liquid gradient is produced in a quartz tube in the dark with an added photo-sensitive solution. An organic cell sample is layered on top of the gradient, the tube and contents are ultracentrifuged, the acrylamide is polymerized with light forming a gel phase which immobilizes bands formed by accumulations of particles of the cell material or viable cells which have been separated. These bands are scanned with an ultraviolet densitometer and compared with a reference tube produced in the same way but without thee added cell sample. Visible patterns of the scanned bands are compared to show variations from standard, changes in previous samples of cellular material from the same patient or otherwise studied and analyzed, as for example, by chemical analysis of the bands cut out from the gel. Staining of the sample can be made to the upper bath of an electrophoretic equipment permitting the stain to run through the tube during electrophoresis. De-staining is accompanied by electrophoresis with acetic acid. Protein and non-protein bands can be identified by contact with specific antibodies after the bands have been formed. A white precipitate forms if an antibody-antigen reaction occurs and subsequently staining with amido Schwartz stain and de-staining with electrophoresis intensifies the bands with color.

It will, therefore, be understood that the invention provides a very effective tool for identification and analysis of organic cells, molecules constituting these cells or material synthesized by the living cells.

It is then an object of this invention to provide a gradient system which develops patterns of biological cellular material useful in analysis and diagnosis.

Another object of the invention is to provide a sucrose-acrylamide gradient system for identification, analysis, and separation of organic cells.

A specific object of this invention is to provide a research tool for separating organic cells and their molecular components into bands that can be analyzed with ultraviolet light.

Another specific object of the invention is to provide a method of analyzing the cells of body fluids to determine or predict pathological conditions of a patient without requiring the services of highly skilled technicians.

Other and further objects of this invention will be apparent to those skilled in this art from the following detailed descriptions and specific examples but it should, of course, be understood that the scope and principals of this invention are not avoided by departures from the specific hereinafter contained description and that alternatives and variations will be available to those skilled in the art without departing from the scope of the herein claimed invention.

EXAMPLE:

A sucrose-acrylamide photo-sensitive gradient is prepared in the dark in a quartz tube, the organic cellular material to be separated and analyzed is layered on top of the pre-formed gradient and the tube is centrifuged at very high speeds. The gradient is in a liquid phase initially but after centrifugation, the acrylamide is polymerized by light forming a gel phase thereby immobilizing bands formed by the accumulation of particles from the specimen being analyzed. Then the cellular material or the viable cells which have been separated are scanned with an ultraviolet densitometer and it is not necessary to use stains to identify the bands. A specific technique involves the preparation of the following solutions:

| MATERIALS: | | | |
|---|---|---|---|
| 1. | Solution A: | | 48.0 ml 1N HCl (Use 100 ml vol. flask) |
| | | | 36.3 ml TRIS (2-amino-2-(hydroxymethyl) - 1, 3 propanediol) |
| | | | 0.23 ml TEMED (tetramethylethylene-diamine) |
| | | | Add water to make 100 ml. |
| 2. | Solution C: | | 60.0 g Acrylamide |
| | | | 1.6 g Bis acrylamide |
| | | | Add water to make 100 ml. |
| 3. | Solution E: | | 0.2 g Riboflavin |
| | | | Add water to make 100 ml |
| | | | Centrifuge, use cleared sols only. |
| 4. | Aqueous Sucrose Solutions: | | 2.4, 2.1, 1.8, 1.5, 1.2 and 1.0 M. Increments may be increased or decreased and aqueous solutions varying in percentage of sucrose by weight or volume instead of varying molar concentrations may be used. |

PROCEDURE

1. Put into 6 test tubes (10 ml size), 4.0 ml of the 6 different molar sucrose solutions. The solution should be prepared in sufficient amounts for a week's supply.
2. Add 1.0 ml of A and 1.0 ml of C to each of the test tubes. Mix on a shaker in the light.
3. Add 0.2 ml of E to each tube. Since this solution is photosensitive it must be added in the dark. From this step forward, the procedure must be performed in the dark until after centrifugation. If the operator works quickly, the procedure can be performed in the light.
4. Mix all the tubes on the shaker again.

Six syringes with long needles are set up on a stand and quartz tubes, plugged with epoxy imbedded corks, are placed underneath in containers or holders. A linear measurement of the gradients may also be used instead of volume. The linear system increases the speed of preparation. Each quartz tube has a total capacity of 2.0 mls. The plungers are greased with immersion oil to facilitate the ejection of solution from the syringes. First, the 2.4 M solution of sucrose-acrylamide solution is placed in each syringe (1.0 ml). The needle is aimed against the wall of the centrifuge tube and the volume of solution is allowed to flow freely. This solution is then followed by those of decreasing density. Caution must be taken when adding new layers so that the preceeding ones are not disturbed. After all of the solutions have been added, opaque lines which are clearly visible identify the distinct layers of the gradient. The specimen to be studied is placed on the top of the gradient, the tubes are wrapped in rubber tubing, and centrifuged in a Beckman swinging bucket for 60 minutes at 3,000 rpm (800 × $g$). The resilient rubber support in the swinging buckets prevents distortion of the bands that are formed. After centrifugation, the tubes are exposed to fluorescent light for about 20 minutes causing the gradient to solidify. If the specimen is too concentrated, it is diluted 1:1 with the 1.0 M sucrose solution. Usually the 1.0 M sucrose-acrylamide solution is not part of the gradient, but is used as a diluent for the specimen. After the gel is formed, the tube is placed in an ISCO gel scanner, Model 65 with Type 6 optical unit and Model UA 5 Absorbance Monitor and scanned with ultraviolet light, with a reference tube prepared in the same way as the sample tube but with water instead of the sample.

The patterns formed by the bands of molecules or cells immobilized in the gel phase are recorded to form a pattern which can be compared to previous studies of the same individual or a predetermined normal pattern. Storage of the recordings on tapes is useful for comparative studies.

The method of this invention avoids heretofore cumbersome identification of sucrose gradients wherein the material could not be scanned and identification of the material is made chemically after removal from the tube drop by drop. The present method makes possible analysis without removal from the quartz centifuge tubes. The entire process from preparation of gradients to scanning and recording can be automated so that many samples can be studied continuously with minimal untrained technical help.

Variations

The method has been expanded in the following ways:

1. The concentration of the acrylamide described above is 7%, however, different concentrations from approximately 5–11% by weight can be used. A decrease in concentration causes an increase in pore size so that larger cells or molecules can pass through the gradient during centrifugation. The reverse holds for increased concentrations.
2. Changes in concentrations of sucrose and a decrease or increase of layers can be made for greater definition of bands.
3. Dialysis of serum or urine through membranes of known pore size, then concentrated through freeze-vacuum, has been used to isolate mini-molecules of less than 3500 MW and to prevent interference by macro-molecules during centrifugation.
4. Use of ammonium persulfate instead of vitamin E (Riboflavin) to polymerize acrylamide has been satisfactory.
5. The gradients need not be made up in the dark as indicated above if the prepared solutions are wrapped in aluminum foil and the gradients covered with foil. This technique is useful if the process must be slowed down for any reason. Usually the gradient takes only a few minutes to prepare and no gel is formed within this short period of time.

Uses

1. Study of urine containing cells and/or molecules and after processing, the normal individuals can be separated from those having a pathological condition.
2. Study of patients undergoing therapy of various diseased conditions such as dialysis patients or kidney transplant patients. Patterns of their serum or urine or both may predict a crisis or used to monitor between treatments since protein molecules and cells vary in serum and urine depending on the patients condition and treatment given.
3. Scanning of normal individuals over a period of time before they develop abnormal conditions. If the patterns of their body fluids is known, the development of a pathological condition could be detected at an early stage. This technique can be used to identify an early stage of cervical cancer since this pathological condition takes many years to develop. Cancer cells are heavier than normal cells which whenn recorded would shift the usual normal pattern in the recording. Highly skilled technicians are used now to process cervical specimens for the Pap test to test for cancer or other abnormal conditions. However, these technicians are in short supply and they are not able to handle that vast number of individuals who should be studied periodically, or even those thought to be in jeopardy or who are admitted in our hospitals today for other reasons.

STUDIES MADE

1. As a monitoring system:
  a. Obtained patterns of the molecules and cells excreted from urological patients that had various conditions and those that had kidney transplants. Patients that were beginning to reject their transplanted kidneys produced an extra band than those not rejecting. This system may be useful to predict rejection of kidney transplants before they happen.

b. The system can detect mini-protein molecules excreted by patients with abnormal urological conditions. It can be used as a system for detection and effect of treatment and subsequent prognosis. Mini-Molecules cannot be detected with present systems.

c. The system can be used to monitor the blood or patients before and after blood dialysis and thus possibly indicate adequate treatment or predict a crisis before clinically evident.

2. To study cellular characteristics:

a. Isolation of three different types of lymphocytes in tissue culture showing use of the method as a monitoring technique in the production of mammalian cells. It can also be used to obtain patterns of white cell populations in patients with blood abnormalities.

b. Obtained different patterns of yeast cells that were cultured in different media and that were treated in different ways. The technique is so sensitive that it was possible to differentiate between well fed and "starved" yeast cells.

3. As a screening system:

a. Recorded patterns of urines obtained from test animals receiving chemotherapy, usually given to human patients with cancer, to determine the lethal and destructive effect of the drugs. Therefore, this system may be used to screen for effects of chemotherapy in other animals before use in humans.

b. Recorded patterns of urines obtained from patients with cancer of the breast, colon, cervix and so forth, with and without metastasis. The patterns were not similar or identical to patterns obtained from normal individuals. Therefore, this method may be used as a screening method to detect patients with other types of cancer other than that of the excretory system.

From the above descriptions, it should be understood to those skilled in this art that this invention provides a very useful (1) monitoring system, (2) research tool in the study of organic cells and molecules (3) and screening system.

I claim as my invention:

1. A method of studying organic cells and molecules which comprises layering photosensitive sucrose-acrylamide solutions of decreasing density in a quartz centrifuge tube, placing a specimen of organic material to be studied on top of the layered solutions, centrifuging the quartz tube and contents to separate constituents of the specimen into the various layers of the solution, exposing the quartz tube and contents to light until the solution is solidified, scanning the resulting gel with ultraviolet light to obtain patterns formed by bands of molecules or cells from the sample that are immobilized in the gel, and recording the bands which form patterns for comparative study.

2. The method of claim 1, wherein the photosensitive acrylamide sucrose solutions of decreasing density are prepared from aqueous hydrochloric acid solutions of tris(-2-amino-2-(hydroxymethyl)-1, 3, propanediol) and tetramethylethylenediamine, an aqueous solution of acrylamide and bis acrylamide, an aqueous riboflavin solution and a plurality of aqueous sucrose solutions of varying concentrations.

3. The method of claim 2, wherein the sucrose solutions for the various layers decrease in density from 2.4 to 1 Molar.

4. The method of claim 1 wherein the concentration of the acrylamide solution is from 5 to 11 % by weight.

5. The method of claim 1 wherein the organic material is a body fluid.

6. The method of claim 5 wherein the body fluid is urine.

7. The method of claim 5 wherein the body fluid is first dialyzed through a membrane and then concentrated by freezing under vacuum.

8. The method of detecting a pathological condition which comprises layering photosensitive sucrose-acrylamide solutions of decreasing densities, placing a specimen of a body fluid on the layered solutions, ultracentrifuging the specimen containing solutions to separate the cell constituents of the specimen into the various layers, gelling the layered solution with fluorescent light to form bands of the separated constituents of the body fluid in the layers, scanning the bands with ultraviolet light and comparing the band patterns with similar bands of a control specimen.

9. The method of claim 8 including recording the band patterns for future comparison with subsequent specimens from the same patient.

10. The method of claim 8 wherein the layered solutions are formed in quartz tubes and the specimen is injected with needles into the tubes.

11. The method of claim 10 wherein the tubes are plugged with epoxy resin treated corks to prevent leakage during the ultracentrifugation.

12. The method of claim 10 wherein the tubes are wrapped in foil to exclude light prior to the fluorescent light exposure.

13. The method of claim 10 wherein the quartz tubes are wrapped in rubber tubing and supported in swinging buckets during ultracentrifugation to prevent distortion of the bands.

14. The method of claim 1 wherein the specimen is a body fluid and successive specimens from the same patient are similarly layered and gelled and the patterns of the bands, molecules or cells form the specimen are successively compared to monitor the condition of the patient.

* * * * *